US012773487B2

(12) United States Patent
Tate

(10) Patent No.: US 12,773,487 B2
(45) Date of Patent: *Oct. 27, 2026

(54) SYSTEM AND METHOD FOR ELECTROCHEMICALLY FILTERING A BODILY FLUID IN THE TREATMENT OF ALZHEIMERS DISEASE AND OTHER DISEASES

(71) Applicant: John O. Tate, Lincoln, RI (US)

(72) Inventor: John O. Tate, Lincoln, RI (US)

( * ) Notice: Subject to any disclaimer, the term of this patent is extended or adjusted under 35 U.S.C. 154(b) by 292 days.

This patent is subject to a terminal disclaimer.

(21) Appl. No.: 18/612,189

(22) Filed: Mar. 21, 2024

(65) Prior Publication Data

US 2024/0261486 A1 Aug. 8, 2024

Related U.S. Application Data

(63) Continuation-in-part of application No. 18/314,930, filed on May 10, 2023, now Pat. No. 11,944,736, which is a continuation-in-part of application No. 17/831,205, filed on Jun. 2, 2022, now abandoned.

(60) Provisional application No. 63/321,830, filed on Mar. 21, 2022, provisional application No. 63/298,367, filed on Jan. 11, 2022.

(51) Int. Cl.
*A61M 1/36* (2006.01)

(52) U.S. Cl.
CPC .......... *A61M 1/3689* (2014.02); *A61M 1/367* (2013.01); *A61M 2202/0042* (2013.01); *A61M 2202/0445* (2013.01); *A61M 2202/0464* (2013.01)

(58) Field of Classification Search
CPC ................ A61M 1/3689; A61M 1/367; A61M 2202/0445; A61M 2202/0464; A61M 2202/07; A61M 2210/0693; A61M 1/36
See application file for complete search history.

(56) References Cited

U.S. PATENT DOCUMENTS 5,882,325 A 3/1999 Plunkett
10,272,188 B1 4/2019 Geiger
11,065,425 B2 7/2021 Lad
(Continued)

FOREIGN PATENT DOCUMENTS

EP 2087916 A1 8/2009
WO 2016024217 A1 2/2016
(Continued)

*Primary Examiner* — Susan S Su
*Assistant Examiner* — Erin A Kim
(74) *Attorney, Agent, or Firm* — Hinckley Allen & Snyder; Stephen Holmes

(57) ABSTRACT

A method for electrochemically filtering a bodily fluid in the treatment of a disease includes a pump to circulate the fluid through a collection container and an electromagnetic charging system. One of the cathode and anode leads is connected to a collection plate while the other of the cathode and anode leads is connected a patient to be treated. Inlet and outlet catheters are connected to patient to be treated. A predetermined voltage is applied across the anode lead and the cathode lead from a DC power supply, wherein circulating fluid from the patient passes through the collection container for removal of charged biological materials onto the collection plate. The fluid is returned back to the patient by the pump system.

11 Claims, 1 Drawing Sheet

(56) References Cited

U.S. PATENT DOCUMENTS

| | | | | |
|---|---|---|---|---|
| 11,944,736 | B2 * | 4/2024 | Tate | A61M 1/36 |
| 2008/0041792 | A1 | 2/2008 | Crnkovich | |
| 2009/0131850 | A1 | 5/2009 | Geiger | |
| 2013/0178834 | A1 | 7/2013 | Greenberg | |
| 2015/0136701 | A1 | 5/2015 | Chait | |
| 2015/0273129 | A1 | 10/2015 | Freeman | |
| 2019/0009014 | A1 * | 1/2019 | Chen | A61M 1/16 |
| 2019/0381070 | A1 | 12/2019 | Brewer | |
| 2020/0147357 | A1 | 5/2020 | Hedstrom | |
| 2021/0001032 | A1 | 1/2021 | Eliaz | |
| 2021/0023293 | A1 | 1/2021 | DePasque | |
| 2021/0220480 | A1 * | 7/2021 | Peyman | A61P 35/04 |

FOREIGN PATENT DOCUMENTS

| | | | |
|---|---|---|---|
| WO | 2021108861 | A1 | 6/2021 |
| WO | 2022067006 | A1 | 3/2022 |

* cited by examiner

SYSTEM AND METHOD FOR ELECTROCHEMICALLY FILTERING A BODILY FLUID IN THE TREATMENT OF ALZHEIMERS DISEASE AND OTHER DISEASES

CROSS-REFERENCE TO RELATED APPLICATIONS

This application is a continuation-in-part of U.S. patent application Ser. No. 18/314,930, filed May 10, 2023, now U.S. Pat. No. 11,944,736 issued Apr. 2, 2024, which is a continuation-in-part of U.S. patent application Ser. No. 17/831,205, filed Jun. 2, 2022 (now abandoned), and which is related to and claims priority from U.S. Provisional Patent Application No. 63/321,830, filed Mar. 21, 2022, and U.S. Provisional Application No. 63/298,367, filed Jan. 11, 2022, the entire contents of which are fully incorporated herein by reference.

BACKGROUND OF THE DISCLOSURE

Field of the Invention

The present disclosure relates generally to methods for treating Alzheimer's disease and more particularly to a method of electrochemically removing charged biological materials, such as charged proteins and cells, from the blood stream or from fluids circulating in and around brain tissues.

Background of the Invention

Alzheimer's is a type of dementia that affects memory, thinking and behavior. Symptoms are progressive and eventually grow severe enough to interfere with daily tasks. In early stages of Alzheimer's disease memory loss is mild, but with late-stage Alzheimer's, individuals lose the ability to carry on a conversation and respond to other people and their environment. Alzheimer's is a contributing factor to and/or the sixth-leading cause of death in the United States. On average, a person with Alzheimer's lives 4 to 8 years after diagnosis but can live as long as 20 years, depending on other factors. Alzheimer's has no cure, but there is ongoing research into the potential for pharmaceutical therapies to remove amyloid plaques, one of the hallmarks of Alzheimer's disease. It is believed that the plaques interfere with electrochemical communication of neurons and therefore the removal of such plaques from the brain may be reasonably likely to reduce cognitive impairment and functional decline in people living with early Alzheimer's. Experimental monoclonal antibody treatments that reduce amyloid plaques have demonstrated some effectiveness, but such treatments are extremely expensive.

Because of the devastating effects on the lives of tens of thousands of patients diagnosed with Alzheimer's each year, there is a worldwide effort underway to find better ways to treat the disease, delay its onset and/or prevent it from developing.

BRIEF SUMMARY OF THE DISCLOSURE

Methods for removing charged proteins and cells from the brain, spinal fluid, tissue and blood stream may be one effective treatment modality for improvement of cognitive impairment and the treatment of other diseases.

In this regard, it is an objective of the present disclosure to provide a means by which the body's natural electrochemical state can assist with an electromagnetic deposition system to remove plaque from brain tissues, blood and spinal fluid, and to remove other charged biological materials from the bloodstream.

Amyloid plaque and neurofibrillary tau tangles are two protein molecules that are naturally occurring in the brain, blood and spinal fluid. It is reasonably certain that the accumulation of these proteins disrupts the part of the brain cells that channel the distribution of electrical signals. Extracorporeal removal of pathogens or pathogen-related molecules is an upcoming scientifically investigated adjunct to the current palette of treatment options for known blood diseases and infections. Several membranes and filters with specific binding profiles for various molecules and proteins are currently available for clinical use in available blood filtering systems. Extracorporeal blood Aβ (amyloid-beta) removal systems (E-BARS) have been suggested as a way of removing amyloid proteins from the blood by dialysis. As noted above, there is ongoing research that suggests that removing these proteins may be a way of reducing Alzheimer's symptoms. In theory, rapid removal of blood Aβ reduces Aβ concentrations in the blood, which might accelerate Aβ transport from the brain into the blood thus reducing levels of amyloid in the brain.

The present disclosure proposes an electrochemical removal method. As generally known in electrochemical processes, current flows from a positive (anode) to a negative (cathode). In a system having a positively charged body and a blood or other fluid containing positively charged plaques or proteins, the positively charged particles will be electrochemically attracted to a cathode for removal. A cathode plate contained in a collection vessel where blood or spinal fluid is circulated could be utilized to electrochemically remove plaque or protein particles from the circulating fluid.

In the present disclosure, blood, spinal fluid or a brain cavity flushing fluid may be circulated into and outside of the body (extracorporeally) by means of blood pumps or other external circulatory systems. While passing through the pumping system, the amyloid plaques and tau tangles are filtered (electrochemically removed) from the blood/fluids which are then returned to the body with lower the protein levels, and in the process, reduce symptoms.

In a first embodiment a patient's blood is filtered using a pump to circulate the blood from the patient to the collection vessel where an electrical current will cause anything that has a positive charge to be attracted to a cathode plate suspended in the collection vessel for later disposal.

In an alternate embodiment for removing the proteins from the patient's spinal fluid, a pump operates to circulate a flushing fluid through the cranial cavity. The pump will circulate the solution from the collection vessel to the patient. Since the solution has a negative charge (cathode), plaque/protein, which may be free floating in the spinal fluid or which may be attached to the brain cells is charged positive (anode), the plaque will be electrochemically attracted to the cathode and delivered to the metal cathode plate in the collection vessel.

It is therefore an object to provide for an effective method of removing amyloid plaques from the blood stream. It is a further object to provide for an effective method of removing tau tangles from the blood stream. It is still a further object to provide an electromechanical method of removing amyloid plaques and tau tangles from the blood stream or from fluids circulating in and around brain tissues.

In another exemplary embodiment, cancer cells are well-known to secrete a large amount of anions across plasma membranes as a hallmark. Studies have revealed that this hallmark may lead to a generation of unique negative charges on the surfaces of cancer cells. In the reverse of the above-described electrochemical processes, blood or other fluid containing negatively charged proteins or other biological materials (negatively charged cancer cells), the negatively charged materials will be electrochemically attracted to a cathode for removal. A cathode plate contained in a collection vessel where blood or spinal fluid is circulated could be utilized to electrochemically remove cancer materials from the circulating blood/fluid.

These together with other objects of the disclosure, along with various features of novelty that characterize the disclosure, are pointed out with particularity in the claims annexed hereto and forming a part of this disclosure. For a better understanding of the disclosure, its operating advantages and the specific objects attained by its uses, reference is made to the accompanying drawings and descriptive matter in which there are illustrated exemplary embodiments.

BRIEF DESCRIPTION OF THE DRAWINGS

In the drawings which illustrate the best mode presently contemplated for carrying out the present disclosure.

DETAILED DESCRIPTION OF THE EXEMPLARY EMBODIMENTS

Figure 2:
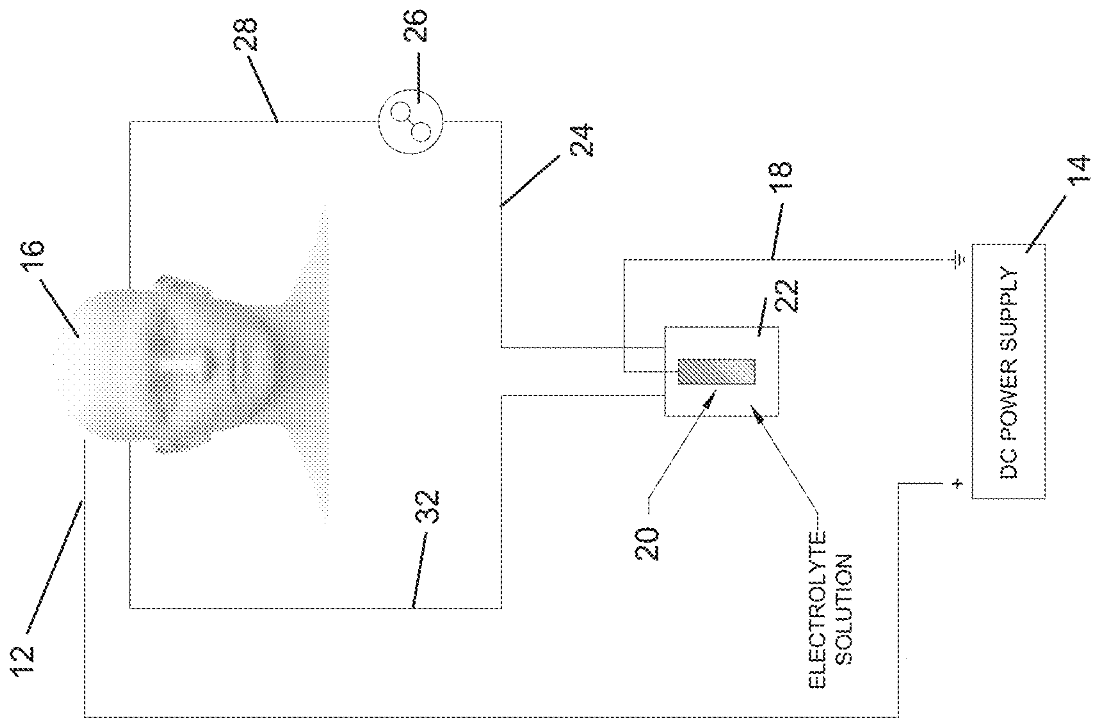
FIG. 2 is a schematic illustration of a method and system for filtering and removing charged biological materials from the brain fluid and/or spinal fluid of a patient.
Figure 1:
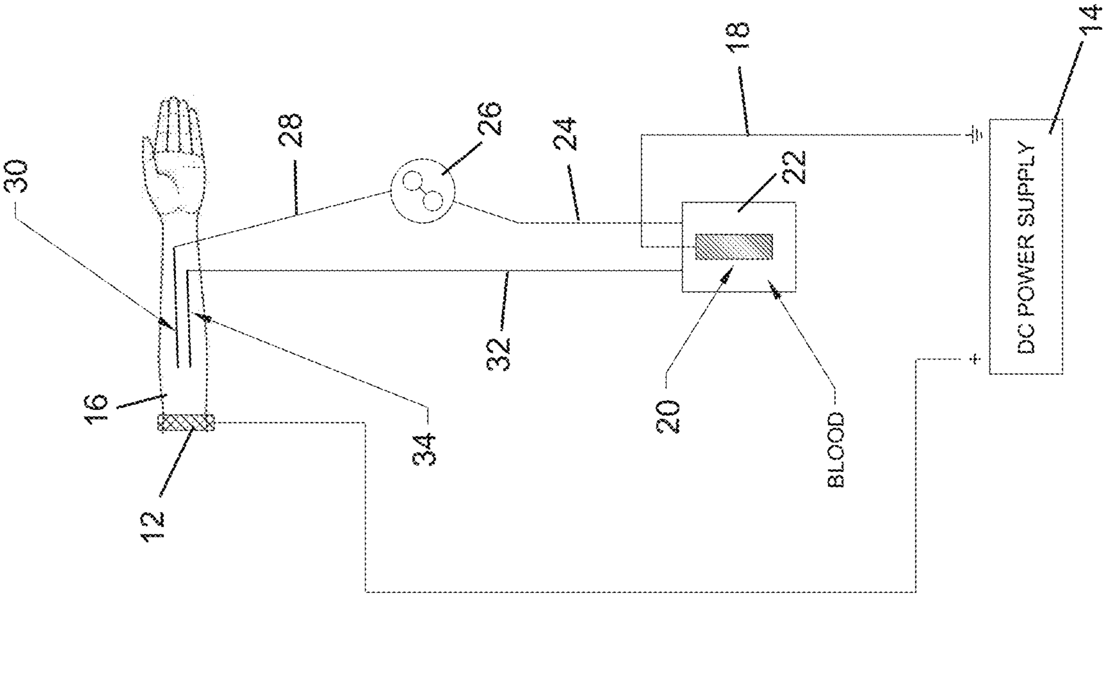
FIG. 1 is a schematic illustration of a method and system for filtering and removing charged biological materials from the blood stream of a patient.

Now referring to the drawings, FIGS. 1 and 2 illustrate generally a method and system for treating Alzheimer's disease and more particularly an electrochemical method of removing amyloid plaques and tau tangles from the blood stream or from fluids circulating in and around brain tissues. As will be described in further detail below, in a first embodiment a patient's blood is filtered using a pump to circulate the blood from the patient to the collection vessel where an electrical current will cause anything that has a positive charge to be attracted to a negative cathode plate suspended in the collection vessel for later disposal. In an alternate embodiment for removing amyloid from a patient's brain and/or spinal fluid, a pump operates to circulate a flushing fluid. The pump will circulate the solution from the collection vessel to the patient.

The present disclosure provides a means by which the body's natural electrochemical state can assist with an electrochemical deposition system for the removal of plaque from the brain, blood and spinal fluid. Amyloid plaque and tau tangles are two protein molecules that are naturally occurring in the brain, blood and spinal fluid. It is reasonably certain that the accumulation of these proteins disrupts the part of the brain cells that channel the distribution of electrical signals. As noted above, there is ongoing research that suggests that removing these proteins may be a way of reducing Alzheimer's symptoms.

As generally known in electrochemical processes, current flow is from positive (anode) to negative (cathode). It is known that plaques and proteins are positively charged. The system of the present disclosure employs a negatively charged collection body (cathode) over which blood or other fluid containing the positively charged plaques (proteins) are transported. As a result, the positively charged particles are electrochemically attracted to the cathode for removal to a cathode plate contained in a collection vessel.

Extracorporeal removal of pathogens or pathogen-related molecules is an upcoming scientifically investigated adjunct to the current palette of treatment options for known blood diseases and infections. Several membranes and filters with a specific binding profile are currently available for clinical use in available blood filtering systems.

In the present disclosure, blood, spinal fluid or a brain cavity flushing fluid may be circulated into and outside of the body (extracorporeally) by means of blood pumps or other external circulatory systems. While passing through the pumping system, the amyloid plaques and tau tangles are filtered from the fluids and returned to the body lowering the protein levels, and in the process, reduce symptoms.

Turning now to FIG. 1, a first method and system is illustrated for the filtering of blood. A positive lead (anode) 12 extending from a low voltage/low current DC power source 14 positive lead (anode), is connected to the patient's body 16. A negative lead (cathode) 18 also extends from the low voltage/low current DC power source 14 and is connected to a metal plate 20 suspended from the center of a collection vessel 22.

Two ports are provided in the collection vessel, one port contains an IV tube 24 connected to the inlet for a pump 26. Another IV tube 28 is connected to an outlet of the pump 26 and then to the patient's vein 30. The other port contains an IV tube 32 connected to an artery 34. It should be appreciated that while two IV tubes 24, 28 are described many pumps 26 operate such that a continuous IV tube is directed through the pump body and as such the IV tubes 24, 28 may be a single continuous IV tube.

In some embodiments, a positron emission tomography dye (PET) imaging marker may be added to the patient's blood that binds to the plaques to be removed to facilitate the removal of plaque and imaging to confirm the plaque has been removed.

In operation, the pump 26 circulates blood from the patient 16 to the collection vessel 22. The current at the anode 18 plate 20 causes anything that has a positive charge (patient is the anode) to be attracted to the cathode plate 20 suspended in the collection vessel 22 for later disposal. Since the travel of direct current is from positive (anode) to negative (cathode), any debris (plaques, proteins, etc.) attached to the body organs not belonging there, will be electromagnetically attracted to the cathode 18 plate 20 suspended in the collection vessel 22.

Turning now to FIG. 2, an alternate method and system is illustrated for the filtering and or flushing of brain and/or spinal fluid.

A positive lead (anode) 12 extending from a low voltage/low current DC power source 14 positive lead (anode), is connected to the patient's body 16, preferably at the patient's head. A negative lead (cathode) 18 also extends from the low voltage/low current DC power source 14 and is connected to a metal plate 20 suspended from the center of a collection vessel 22.

Two ports are provided in the collection vessel, one port contains an IV tube 24 connected to the inlet for a pump 26. Another IV tube 28 is connected to an outlet of the pump 26 and then to a first hole drilled in the patient's skull to allow electrolytic flushing solution to enter. The other port contains an IV tube 32 connected to a second hole drilled in the patient's skull thereby allowing exit of the flushing fluid. It should be appreciated that while two IV tubes 24, 28 are described many pumps 26 operate such that a continuous IV tube is directed through the pump body and as such the IV tubes 24, 28 may be a single continuous IV tube.

In some embodiments, a positron emission tomography dye (PET) imaging marker may be added to the flushing fluid that binds to the plaques to be removed to facilitate the removal of plaque and imaging to confirm the plaque has been removed.

In operation, the pump 26 circulates electrolyte solution to the patient 16 to flush the plaques and proteins to the collection vessel 22. The current at the anode 18 plate 20 causes anything that has a positive charge (patient is the anode) to be attracted to the cathode plate 20 suspended in the collection vessel 22 for later disposal. Since the travel of direct current is from positive (anode) to negative (cathode), any debris (plaques, proteins, etc.) attached to the body organs not belonging there, will be electrochemically attracted to the cathode 18 plate 20 suspended in the collection vessel 22.

After this procedure is completed, a suction drain is employed to remove the electrolyte solution and the brain is flushed clear of liquid.

Referring again to FIGS. 1 and 2, and in another exemplary embodiment for treating cancer, it is well-known that cancer cells secrete a large amount of anions across cell plasma membranes. Studies have revealed that this hallmark leads to a generation of unique negative charges on the surfaces of cancer cells. In the reverse of the above-described electrochemical system, blood or other fluid containing negatively charged proteins or other biological materials (negatively charged cancer cells), the negatively charged materials will be electrochemically attracted to a charged collection plate for removal. A charged plate contained in a collection vessel where blood or spinal fluid is circulated could therefore be utilized to electrochemically remove cancer materials from the circulating blood/fluid. The circulating system and components of FIGS. 1 and 2 are the same within this methodology Electrochemical Parameters for Operation Electrochemical processes are by their nature an art form that require some level of skill and experience to arrive at suitable electrical parameters and time parameters that are dependent on chemistry, size of the objects, degree of treatment, etc.

Electrical safety parameters are well-known for the human body. The degree of harm to the human body from electric shock depends mainly on the size of the current through the human body and the length of the energized time. The smallest current value that can cause a person to feel is called the perception current, which for DC current, is known to be 5 mA. This value presents an upper limit for current as the treatment would need to be comfortable for an extended period of time.

According to Ohm's law (I=U/R), we can learn that the size of the current flowing through the human body is related to the applied voltage and the resistance of the human body. Since there are many diverse factors for each person, tissue or fluid, the size of the current flowing through the human body or fluid cannot be calculated or known in advance. Therefore, to determine minimum safety conditions, the safety "current" is not often used, but rather a safety "voltage" is used.

Considering the maximum resistance of the human body, we have established a maximum voltage of about 36V. A combination of voltage under 12V and current under 5 mA would be considered suitable and safe. Human body size, bone density, body fat etc. are all factors that will need to be considered and possibly varied within the treatment modality.

Preliminary working parameters are therefore established as follows:

DC Voltage between 0 and 36V with a preferred range of 6-18V and a more preferred range of 8-14V.

DC Amperage between 0 and 5 mA with a preferred range of 2-4 mA.

The present disclosure thus provides an effective method of removing amyloid plaques and/or tau tangles from the blood stream. Further, the present disclosure provides an electromechanical method of removing amyloid plaques and tau tangles from the blood stream or from fluids circulating in and around brain tissues. The present disclosure still further provides an effective method of removing charged biological materials from the blood stream or other bodily fluids. For these reasons, the present disclosure represents a significant advancement in the art, which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described, except insofar as indicated by the scope of the appended claims.

What is claimed:

1. A method for electrochemically filtering a bodily fluid in the treatment of a disease, comprising:

providing a system comprising:

a DC power supply with an anode lead and cathode lead extending therefrom;

a collection container having an inlet with inlet tubing extending therefrom, an outlet with outlet tubing extending therefrom and a collection plate therein; and a pump to circulate a fluid through said collection container;

connecting one of the cathode and anode leads to said collection plate;

connecting the other of the cathode and anode leads to a patient to be treated;

connecting said inlet and outlet tubing to said patient to be treated;

applying a predetermined voltage across said anode lead and said cathode lead from said DC power supply, wherein said predetermined voltage is in a range of greater than 0 and up to and including 36V and wherein a resulting amperage is equal to or less than 5 mA;

circulating said fluid from said patient through said collection container for removal of charged biological materials on said collection plate; and returning said fluid back to said patient.

2. The method of claim 1, wherein said circulating fluid is selected from the group consisting of: blood, brain fluid, and spinal fluid.

3. The method of claim 1, wherein treatment of said fluid comprises passing said fluid over said collection plate wherein a negative charge on said collection plate attracts positively charged biological materials from said fluid.

4. The method of claim 3 wherein said biological materials comprise positively charged proteins.

5. The method of claim 4, wherein said positively charged proteins comprise amyloid plaques and/or tau tangles.

6. The method of claim 1, wherein treatment of said fluid comprises passing said fluid over said collection plate wherein a positive charge on said collection plate attracts negatively charged biological materials from said fluid.

7. The method of claim 6, wherein said negatively charged biological materials comprise cancer cells.

8. The method of claim 1, wherein said fluid is blood and said inlet tube is connected to an artery in the patient to be treated and said outlet tube is connected to a vein of the patient to be treated.

9. The method of claim 1, further comprising:

adding a positron emission tomography (PET) dye to the circulating fluid, wherein said PET dye binds to protein particles allowing confirmation of their removal.

10. The method of claim 1 wherein said predetermined voltage is between 6V and 18V.

11. The method of claim 8 wherein said predetermined voltage is between 8V and 14V.

* * * * *